United States Patent [19]

Janata et al.

[11] Patent Number: 4,776,944
[45] Date of Patent: Oct. 11, 1988

[54] CHEMICAL SELECTIVE SENSORS UTILIZING ADMITTANCE MODULATED MEMBRANES

[76] Inventors: Jiri Janata, 2231 Logan Ave., Salt Lake City, Utah 84108; Robert J. Huber, 1145 E. Millbrook Way, Bountiful, Utah 84010; Michael Thompson, 3642 S. 2500 E., Salt Lake City, Utah 84109

[21] Appl. No.: 92,159

[22] Filed: Sep. 1, 1987

Related U.S. Application Data

[63] Continuation of Ser. No. 841,872, Mar. 20, 1986, abandoned.

[51] Int. Cl.$^4$ ............................................. G01N 27/30
[52] U.S. Cl. ................................... 204/415; 204/418; 204/412; 204/403; 357/25
[58] Field of Search ............... 204/403, 435, 412, 415, 204/416, 418; 357/25; 435/817

[56] References Cited

U.S. PATENT DOCUMENTS

| | | | |
|---|---|---|---|
| 3,799,743 | 3/1974 | Alexander et al. | 204/296 X |
| 4,053,381 | 10/1977 | Hamblen et al. | 204/415 |
| 4,182,667 | 1/1980 | Dobson et al. | 204/416 X |
| 4,214,968 | 7/1980 | Battaglia et al. | 204/418 |
| 4,225,410 | 9/1980 | Pace | 204/412 |
| 4,276,141 | 6/1981 | Hawkins | 204/418 X |
| 4,490,216 | 12/1984 | McConnell | 204/418 X |

OTHER PUBLICATIONS

Thompson et al., "Lipid Membrane . . . Sensing", Analytica Chimica Acta, vol. 47, 1983, pp. 1-21.

Primary Examiner—John F. Niebling
Assistant Examiner—Nam X. Nguyen
Attorney, Agent, or Firm—Thorpe, North & Western

[57] ABSTRACT

A chemical selective sensor system utilizes admittance modulated to detect the presence of chemicals or chemical species in a fluid. The sensor system includes a film or membrane adapted to pass ions when selected chemicals which are to be detected are present at the membrane surface. The membrane is attached to a hydrophilic layer of material which, in turn, is attached to a transformed layer which is deposited on a base substrate. When the selected chamicals are present in the fluid, the membrane interacts with the chemicals to allow ions, also in the fluid, to permeate the membrane. This ion current in the membrane is transformed or converted by the transformer layer to an electronic current which is measured by an electrical circuit coupled to the transformer layer of material. An alternating current source is coupled at one terminal to the transformer layer and to the measuring circuit, and at another terminal to a circuit return electrode.

20 Claims, 1 Drawing Sheet

CHEMICAL SELECTIVE SENSORS UTILIZING ADMITTANCE MODULATED MEMBRANES

This is a continuation, of application Ser. No. 06/841,872 filed 3/20/86 now abandoned.

BACKGROUND OF THE INVENTION

This invention relates to a solid state electrochemical sensor for selectively sensing chemical species in a fluid.

Solid state electrochemical sensors for detecting, measuring and monitoring chemical species and properties (e.g. ion activity and concentration, concentration of enzymes, substrates, antibodies, antigens, etc.) generally fall into two categories—potentiometric sensors which utilize some type of chemical layer which is sensitive to ions or some neutral molecules (see, for example, U.S. Pat. No. 4,020,830), and amperometric sensors in which a mass transport limited current provides infomation about the concentration of reducible or oxidizable species (see, for example, U.S. Pat. No. 2,913,386). The latter type of sensors typically suffer from lack of selectivity, that is, from an inability to detect the presence of a particular chemical species in a fluid in which other chemical species may also be present. However, in spite of these and other difficulties with presently known solid state electrochemical sensors, there is still a great deal of interest in finding a practical, solid state, miniaturized sensor which can selectively detect the presence of various chemical species.

SUMMARY OF THE INVENTION

It is an object of the present invention to provide a new and improved solid state electrochemical sensor which may selectively detect and measure chemical properties.

It is another object of the invention to provide a compact, accurate, stable and yet easy to manufacture chemical selective sensor.

It is also an object of the invention to provide such a sensor which can be adapted to selectively detect a variety of chemical species.

It is an additional object of the invention to provide an integrated solid state electrochemical sensor for detecting chemical species in either a liquid or gaseous environment.

The above and other objects of the invention are realized in a specific illustrative embodiment thereof which includes a solid state electrochemical sensor which utilizes a film or membrane adapted to pass ions when selected materials, which are to be detected, are present at the membrane surface. In particular, the electrochemical sensor includes a base substrate, and a layer of material attached to the base substrate for producing electrical current in response to the transport of ions to the layer—this layer actually transforms or converts ionic current to electronic current. The magnitude of electronic current developed in the layer of material is equal to the ionic current. Also included is a membrane attached to the layer for transporting ions to the layer from a fluid containing the material or chemical species to be detected. The membrane includes gating molecules which interact with the chemical species to thereby allow ions from the fluid to permeate the membrane. An alternating current source is coupled to the layer of material and also to an electrode which functions as a return electrical path. A detection circuit is coupled to the layer of material and to the alternating current source for detecting electronic current produced in the layer of material and thus for detecting the concentration of the selected chemical species.

BRIEF DESCRIPTION OF THE DRAWINGS

The above and other objects, features and advantages of the invention will become apparent from a consideration of the following detailed description presented in connection with the accompanying drawings in which.

DETAILED DESCRIPTION

Figure 1:
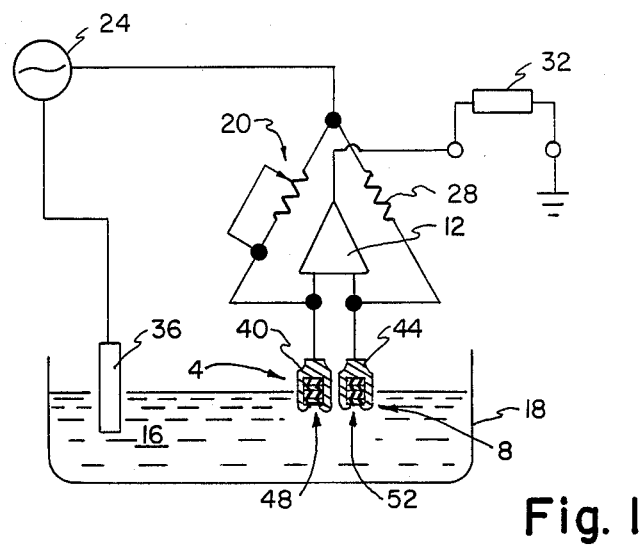
FIG. 1 shows a schematic view of a chemical selective sensor system including an amplifier circuit, made in accordance with the principles of the present invention.

Referring to FIG. 1, there is shown a chemical selective sensor system which includes an active sensor electrode 4 and a reference sensor electrode 8, both coupled to the inputs of a differential amplifier 12. The active sensor electrode 4, which will be discussed in delail later, develops a change in electrical current in response to the presence of certain materials or chemical species in a fluid 16 (held in a container 18) into which the sensor electrode is immersed. The reference electrode 8 develops a current (which may be substantially zero) as a reference against which the current developed by the active sensor electrode may be compared. Although the two electrodes 4 and 8 are shown as being separate, it should be understood that they could be constructed on the same solid state substrate as could the associated circuitry.

The active sensor electrode input of the differential amplifier 12 is also coupled by way of a variable 20 to one side of an alternating current source 24. The reference electrode input of the differential amplifier 12 is coupled by way of a resistor 28 also to the one side of the alternating current source 24. This configuration is a well known bridge differential amplifier circuit. The output of the differential amplifier 12 is coupled to a detection circuit 32 for detecting the level of the output of the amplifier. For example, the detection circuit 32 could be any conventional voltmeter.

To complete the circuit from the alternating current source 24 through the fluid 16 to the active sensor electrode 4, a return electrode 36 is provided and this electrode is coupled to the other side of the alternating current source 24. The return electrode 36 could be made of any type of electrical conductive material such as platinum, a silver/silver chloride compound, etc.

The active sensor electrode 4 and reference electrode 8 are both encapsulated in a fluid impervious coat 40 and 44 respectively so that the fluid 16 contacts the electrodes only through exposed windows 48 and 52. That is, only the outermost layer of each of the electrodes is exposed to the fluid 16.

Figure 2:
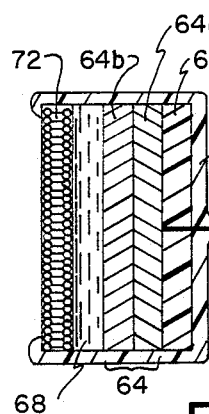
FIG. 2 shows a side, cross-sectional view of the active sensor electrode of the FIG. 1 schematic.

The active sensor electrode 4 of FIG. 1 is shown in a side, cross-sectional view in FIG. 2 in a representative fashion. That is, the thicknesses shown for the different layers is exaggerated for purposes of illustration. The active sensor electrode includes a base substrate 60 upon which the other layers of the sensor are deposited and upon which the electrical components are placed. Attached to the base substrate 60 is a transformer or convertor double layer 64 including an electronic conductor layer of material 64a and a second layer of material 64b. The function of the transformer layer 64 is to convert ionic current, i.e., ions received at the outer surface of the second layer 64b, into electronic current which is applied to an electrical conductor 76 which extends through the base substrate 60 to the metal layer 64a. The layer 64b is a compound capable of both ionic and electronic conduction and capable of exchanging ions with adjacent layers. For example, layer 64a could be silver and layer 64b could be silver chloride. Alternatively, layer 64a could be lead and layer 64b could be lead chloride. It should be mentioned at this point that the chemical or material to be detected is not the ion which will be transported to layer 64b. Rather, such ions are simply the mechanism for determining when the material to be detected is present in the fluid 16. Such material triggers the active sensor electrode to allow the ions in the solution to be transported to the layer 64b. This will be further explained later.

Attached to the transformer layer 64 is a layer of hydrophilic material 68, such as a hydrogel material, e.g., polyhema (poly[hydroxyethyl methacrylate], polyacrylamide, etc. The function of this layer is to provide a stable hydration environment to enable reversible exchange of the transported ion. The layer 68 also provides a suitable surface for deposition of a film or membrane 72 to next be discussed.

The film or membrane 72, which is attached to the layer 68, provides the selectivity enabling detection of certain chemicals or chemical species. This membrane may be either a natural lipid bilayer film obtained from plants or animals or a synthetic phospholipid film produced by the well known Langmuir-Blodgett process. The film could illustratively comprise a phospholipid langmuir-blodgett film made of phosphatidyl chlorine, or could be made of fatty acid. Either the natural or the synthetic film would include so-called gating molecules which control the "opening" and "closing" of the film to the transport of ions. The gating molecules are incorporated onto the membrane 72 by exposing the membrane to a solution containing such molecules. Articles describing lipid membranes of the type used as layer 72 include Thompson, Michael, et al, "Lipid Membrane Dipole Perturbation and Chemoreception as Models for Selective Chemical Sensing", *Analytica Chimica Acta*, Vol. 47, 1983, and Toro-Goyco, E., et al, "Detection of Antisulin Antibodies with a New Electrical Technique: Lipid Membrane Conductometry", *Biochemical and Biophysical Research Communications*, Vol. 23, No. 3, 1966, pages 341–345.

The multilayer active sensor electrode of FIG. 2, as described ealier, is encapsulated in a fluid impervious material 80 to prevent interference with the electrochemical detection process and to prevent corrosion of the layers of the sensor electrode.

An exemplary sensor electrode for detecting acetylocholine is constructed of a silicon wafer base substrate 60 coated with a metallic layer 64a of from 2000 to 5000 angstroms, a sodium tungsten bronze layer 64b of from 2000 to 5000 angstroms, a hydrogel layer 68 of about 10,000 angstroms, and then the membrane or film 72. The gating molecules are acetylcholine receptors which interact with acetylcholine in the fluid 16 to allow sodium ions, also in the fluid (either naturally or artificially), to permeate ("gate" into) the membrane 72.

The system of FIG. 1 detects the presence of certain chemicals or materials in the fluid 16 in the following manner. When the active sensor electrode 4 is placed in the fluid, the chemical to be detected (for example, acetylcholine), binds to the gating molecules on the membrane 72 (for example acetylcholine receptor) and this enables ions in the fluid (for example sodium ions) to permeate the membrane. This permeation or transport of ions in the membrane, which has the effect of increasing the admittance of the membrane, reaches the transformer layer 64 where the ionic current is transformed to an electronic current. If layer 64a is silver and layer 64b is sodium tungsten bronze, then the reaction would be as follows:

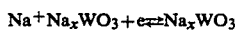

$$Na^+ Na_xWO_3 + e \rightleftarrows Na_xWO_3$$

The electronic current developed in the transformer layer 64 is carried by conductor 76 to the differential amplifier 12, where the difference between that current and the current developed by the reference electrode 8 is amplified and supplied to a current detection circuit 32.

The reference electrode 8 is constructed essentially identical to the active sensor electrode 4 except that gating molecules are not provided in the outer film (so that any current which may be developed by the reference electrode does not change when this electrode is subjected to the chemicals to be detected) or the gating molecules in the outer film are irreversibly inhibited so that a substantially fixed reference current is developed regardless of the chemicals or materials present in the fluid 16.

By employment of an alternating current source 24, net chemical changes at each of the layer interfaces are avoided. Further, this avoids potentiometric measuring approach which requires a charge accumulation over time before an accurate reading can be had of the concentration of the chemical to be detected. Use of the alternating current source enables the use of a small amplitude modulation signal (5 to 50 millivolts) which is less than the threshold breakdown voltages of the membrane 72. Finally, with the employment of the alternating current source, the nature of the ionic to electronic current transformer layer is less important in that the gated ion may be sodium and the transformer structure may include a chloride ion material and vice-versa.

Figure 3:
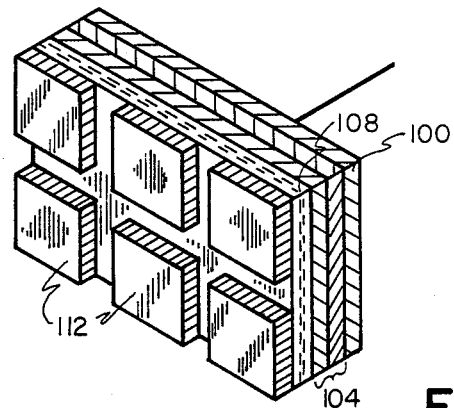
FIG. 3 is a perspective, representational view of a multisensor embodiment made in accordance with the principles of the present invention.

FIG. 3 shows a perspective, representational view of a sensor electrode having multiple sensors. In particular, the electrode includes a base substrate 100, a double transforme layer 104, a hydrophilic layer 108 and a plurality of membranes 112 which are attached to the hydrophilic layer 108 and spatially separated from one another. Each of the membranes 112 would incorporate different gating molecules to enable the detection of different chemicals or chemical species.

Figure 4:
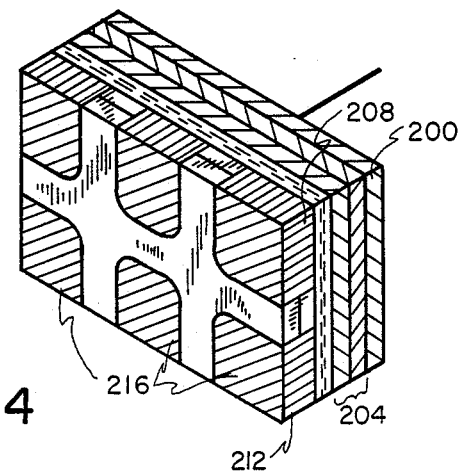
FIG. 4 is a perspective, representational view of a different multisensor embodiment.

FIG. 4 shows an alternative embodiment of a multisensor electrode. This electrode, likewise, includes a base substrate 200, a double transformer layer 204 and a hydrophilic layer of material 208. With this embodiment, however, a single chemical selective membrane or film 212 is provided, with different areas 216 on the membrane surface incorporating different gating molecules, for allowing detection of different chemicals or chemical species. That is, each of the areas 216 on the membrane 212 interact with different chemicals or chemical species to allow permeation of ions into those areas in the membrane 212.

In the manner described for FIGS. 3 and 4, multiple sensors can be provided in a single substrate and used to detect a number of different chemicals or chemical species.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed is:

1. An electrochemical sensor for selectively sensing chemical species of a fluid, said sensor consisting essentially of
   a base substrate,
   a conductor carried by the base substrate,
   a first layer of material attached to the base substrate for producing and supplying electrical current across the boundary between the layer and the base substrate to the conductor in response to transport of ions of a certain species to the layer, where the magnitude of the electrical current produced is equal to the ionic current, said layer being comprised of a compound which includes said certain species,
   a membrane attached to the first layer for transporting ions to the layer, said membrane including gating molecules which selectively interact with the chemical species which is to be detected to thereby allow ions in the fluid to permeate the membrane,
   an alternating current source, one terminal of which is coupled by way of said conductor to the first layer,
   an electrode coupled to the other terminal of the alternating current source, and
   means coupled by way of said conductor to the first layer for detecting the electrical current produced by the first layer.

2. A sensor as in claim 1 further including a fluid impervious material formed about the first layer to prevent contact of the layer with fluid to which the sensor is exposed.

3. A sensor as in claim 1 further including an intermediate layer formed between the first layer and the membrane and comprised of a hydrophilic material.

4. A sensor as in claim 3 wherein said intermediate layer is comprised of a hydrogel material.

5. A sensor as in claim 4 wherein said intermediate layer is comprised of polyhema.

6. A sensor as in claim 4 wherein said intermediate layer is comprised of polyacrylamide.

7. A sensor as in claim 3 wherein said first layer is from about 4000 to 10,000 angstroms in thickness, and wherein said intermediate layer is about 10,000 angstroms in thickness.

8. A sensor as in claim 1 wherein said first layer comprises two sublayers of material, one of which is attached to the membrane and the other of which is electrically coupled to the alternating current source, said one sublayer including said compound.

9. A sensor as in claim 8 wherein said one sublayer is from about 2000 to 5000 angstroms in thickness, and wherein said other sublayer is from about 2000 to 5000 angstroms in thickness.

10. A sensor as in claim 8 wherein said one sublayer is comprised of silver chloride, and said other sublayer is comprised of silver.

11. A sensor as in claim 8 wherein said one sublayer is comprised of sodium tungsten bronze, and said other sublayer is comprised of a metal.

12. A sensor as in claim 11 wherein said electrode and said membrane are disposed adjacent to one another on the base substrate.

13. A sensor as in claim 1 wherein said membrane comprises a phospholipid Langmuir - Blodgett film made of phosphatidyl choline.

14. A sensor as in claim 1 wherein said membrane film is made of fatty acid.

15. A sensor as in claim 1 wherein said electrode and said detecting means are disposed on said base substrate.

16. A sensor as in claim 1 wherein said detecting means comprises
    a differential current amplifier having first and second inputs, the first input being coupled to the first layer,
    first impedance means coupled between said one terminal of the alternating current source and said first input of the differential current amplifier,
    a reference sensor means for producing a reference electrical current and coupled to said second input of the differential current amplifier, and
    second impedance means coupled between said one terminal of the alternating current source and said second input of the differential current amplifier.

17. A sensor as in claim 16 wherein said first impedance means comprises a variable resistor, and said second impedance means comprises a resistor.

18. A sensor as in claim 16 wherein said reference sensor means comprises
    a second layer of material attached to the base substrate at a location spaced from the location of attachment of the first layer, said first and second layers being made of the same material, and
    a second membrane attached to the second layer of material, said first mentioned membrane and said second membrane being made of the same material.

19. A solid state electrochemical sensor for selectively sensing chemical species in a fluid consisting essentially of
    a base substrate,
    a transformer layer of material attached to the base substrate for transforming ionic current received at the layer into electronic current for application across the boundary between the layer and the base substrate, said layer being comprised of a compound which includes said chemical species,
    a plurality of membranes attached to the transformer layer and spatially separated from one another, each for transporting ions to the transformer layer and each including different gating molecules which selectively bind to different chemicals to be detected to thereby allow ions in the fluid to permeate the respective membrane.
    an alternating current source, one terminals of which is coupled to the transformer layer,
    an electrode coupled to the other terminal of the alternating current source, and
    means coupled to the transformer layer for detecting the electronic current developed in the layer.

20. A solid state electrochemical sensor for selectively sensing chemical species in a fluid consisting essentially of
  a base substrate,
  a transformer layer of material attached to the base substrate for transforming ionic current of a certain species received at the layer into electronic current, said layer comprising a compound which includes said species,
  a membrane attached to the transformer layer for transporting ions to the layer, said membrane including gating molecules at a plurality of spaced-apart locations on the membrane, where the gating molecules at each location selectively bind to different chemicals to be detected to thereby allow ions in the fluid to permeate the membrane at the respective location,
  an alternating current source, one terminal of which is coupled to the transformer layer,
  an electrode coupled to the other terminal of the alternating current source, and
  means coupled to the transformer layer for receiving and detecting the electronic current developed in the layer.

* * * * *